United States Patent
Husain

(10) Patent No.: US 10,933,145 B2
(45) Date of Patent: *Mar. 2, 2021

(54) COMPOSITIONS AND METHODS FOR REDUCING THE RISK OF RADIOCONTRAST-INDUCED NEPHROPATHY

(71) Applicant: UNIVERSITY OF PITTSBURGH—OF THE COMMONWEALTH SYSTEM OF HIGHER EDUCATION, Pittsburgh, PA (US)

(72) Inventor: Sohail Husain, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/393,422

(22) Filed: Apr. 24, 2019

(65) Prior Publication Data

US 2019/0247521 A1  Aug. 15, 2019

Related U.S. Application Data

(63) Continuation of application No. PCT/US2017/058568, filed on Oct. 26, 2017.

(60) Provisional application No. 62/413,145, filed on Oct. 26, 2016.

(51) Int. Cl.
| | | |
|---|---|---|
| A61K 49/04 | (2006.01) | |
| A61P 13/12 | (2006.01) | |
| A61K 38/13 | (2006.01) | |
| A61K 31/436 | (2006.01) | |

(52) U.S. Cl.
CPC ........ *A61K 49/0438* (2013.01); *A61K 31/436* (2013.01); *A61K 38/13* (2013.01); *A61K 2123/00* (2013.01); *A61P 13/12* (2018.01)

(58) Field of Classification Search
None
See application file for complete search history.

(56) References Cited

U.S. PATENT DOCUMENTS

| | | |
|---|---|---|
| 2010/0003190 A1 | 1/2010 | Kolyada et al. |
| 2016/0303187 A1 | 10/2016 | McPherson et al. |

FOREIGN PATENT DOCUMENTS

| | | |
|---|---|---|
| WO | WO 2016/191743 A1 | 12/2016 |

OTHER PUBLICATIONS

Jin et al. Exposure to Radiocontrast Agents Induces Pancreatic Inflammation by Activation of Nuclear Factor-kB, Calcium Signaling, and Calcineurin. Sep. 2015 Gastroenterology 149: 753-764. (Year: 2015).*
International Search Report dated Jan. 11, 2018 in International Application No. PCT/US17/58568.

* cited by examiner

*Primary Examiner* — Jennifer Lamberski
(74) *Attorney, Agent, or Firm* — Baker Botts L.L.P.

(57) ABSTRACT

The present invention relates to compositions and methods for reducing the risk and/or extent of radiocontrast-induced nephropathy ("RIN") for kidney-imaging procedures that employ a radiocontrast medium. It is based, at least in part, on the discovery that, in a renal tubular cell line, radiocontrast induced inflammatory upregulation and cell injury could be reduced by calcineurin inhibitors FK506 and cyclosporine.

13 Claims, 4 Drawing Sheets

Figure 1:
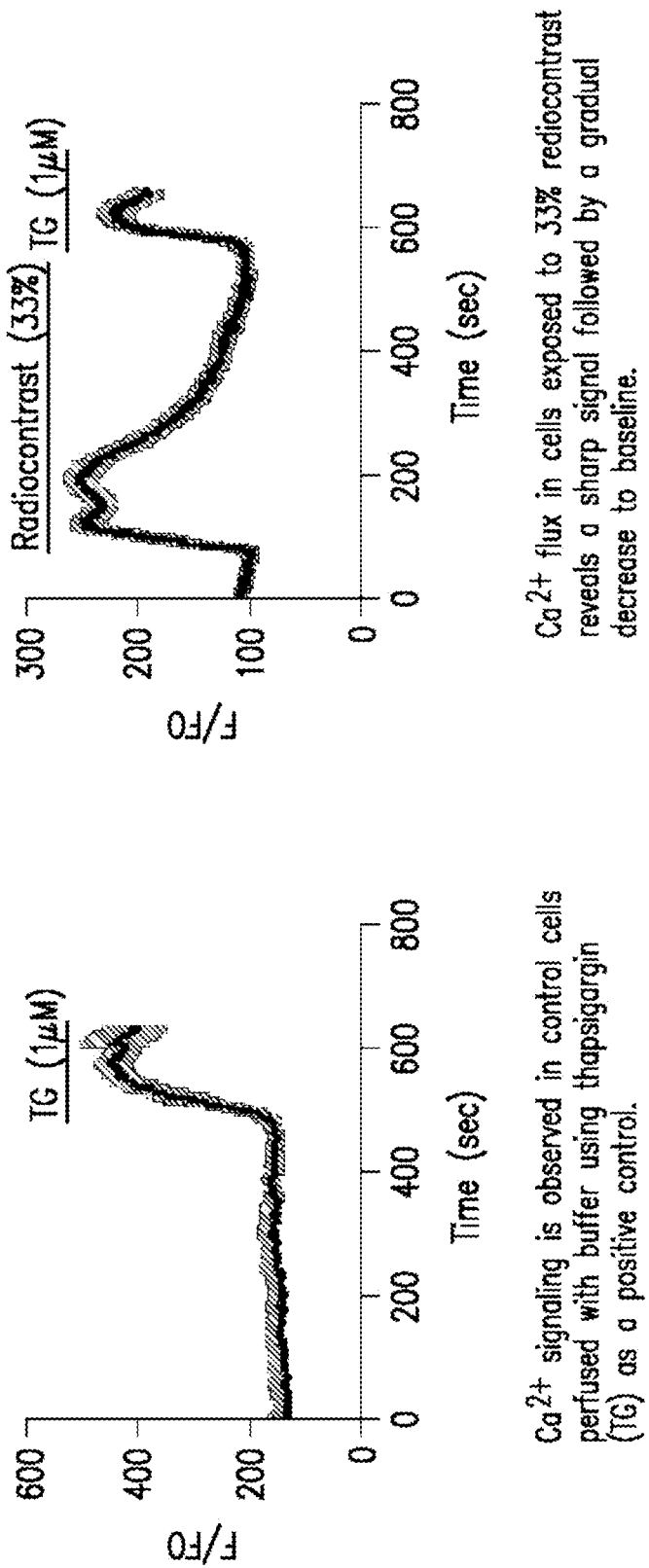

COMPOSITIONS AND METHODS FOR REDUCING THE RISK OF RADIOCONTRAST-INDUCED NEPHROPATHY

CROSS REFERENCE TO RELATED APPLICATIONS

This present application is a continuation of International Patent Application No. PCT/US2017/058568, filed Oct. 26, 2017, which claims priority to U.S. Provisional Patent Application No. 62/413,145, filed Oct. 26, 2016, priority to which is claimed, and the contents of both of which are incorporated by reference herein in their entireties.

GRANT INFORMATION

This invention was made with government support under Grant No. 1R01 DK093491 awarded by the National Institutes of Health. The government has certain rights in the invention.

1. INTRODUCTION

The present invention relates to compositions for use in, or in conjunction with, kidney imaging studies which decrease the risk and/or extent of radiocontrast-induced nephropathy.

2. BACKGROUND OF THE INVENTION

Radiocontrast, particularly iodinated radiocontrast, is used widely in a host of medical imaging procedures, including CT scanning and various types of fluoroscopy (e.g., angiography, biliopancreatography and myelography). Radiocontrast-induced nephropathy ("RIN") is defined as the emergence of acute kidney injury soon after radiocontrast administration. RIN is a major problem for which current preventatives are of limited benefit. RIN is the third leading cause of hospital-acquired acute kidney injury and accounts for one third of acute kidney injuries in the hospital setting. The incidence may be as high as 30 percent in patients with preexisting risk factors and up to 10 percent in patients without pre-existing risk factors. RIN also leads to substantial mortality and morbidity, including permanent renal insufficiency and the need for dialysis. The reason why patients are at particular risk for RIN with radiocontrast exposure is that the radiocontrast is excreted by the kidneys and gets concentrated in the renal tubules before exiting the body. Several mechanisms have been attributed to RIN, including toxicity from hypoxia, oxidative stress, and the hyperviscosity or hyperosmolality of the concentrated radiocontrast. However, antioxidant prophylaxis and overhydration with intravenous crystalloids have provided only modest benefit.

3. SUMMARY OF THE INVENTION

The present invention relates to compositions and methods for reducing the risk and/or extent of radiocontrast-induced nephropathy ("RIN") for kidney-imaging procedures that employ a radiocontrast medium. It is based, at least in part, on the discovery that, in a renal tubular cell line, radiocontrast induced inflammatory upregulation and cell injury could be reduced by calcineurin inhibitors FK506 and cyclosporine.

In non-limiting embodiments, the invention provides for a radiocontrast medium comprising: (i) a radiocontrast agent; and (ii) a calcineurin inhibitor. In related non-limiting embodiments, said radiocontrast medium may be used in performing imaging of the kidney with decreased risk and/or extent of subsequent nephropathy relative to conventional radiocontrast media that lack a calcineurin inhibitor.

In certain embodiments, the present invention further provides for methods for reducing the risk and/or extent of RIN by the administration of a radiocontrast medium that comprises: (i) a radiocontrast agent; and (ii) a calcineurin inhibitor.

The present invention is unexpected in view of the nephrotoxicity associated with acute administration of calcineurin inhibitors. According to certain embodiments, the invention provides said inhibitors at concentrations below those associated with nephrotoxicity.

4. BRIEF DESCRIPTION OF DRAWINGS

FIG. 1A-B. (A) Calcium signaling in MDCK (Madin-Darby Canine Kidney) control cells perfused with buffer, where thapsigargin was administered at the timepoint shown as a positive control. (B) MDCK cells exposed to 33 percent contrast reveals a sharp signal followed by a gradual decrease to baseline. Thapsigargin was administered at the timepoint shown as a positive control.

Figure 2:
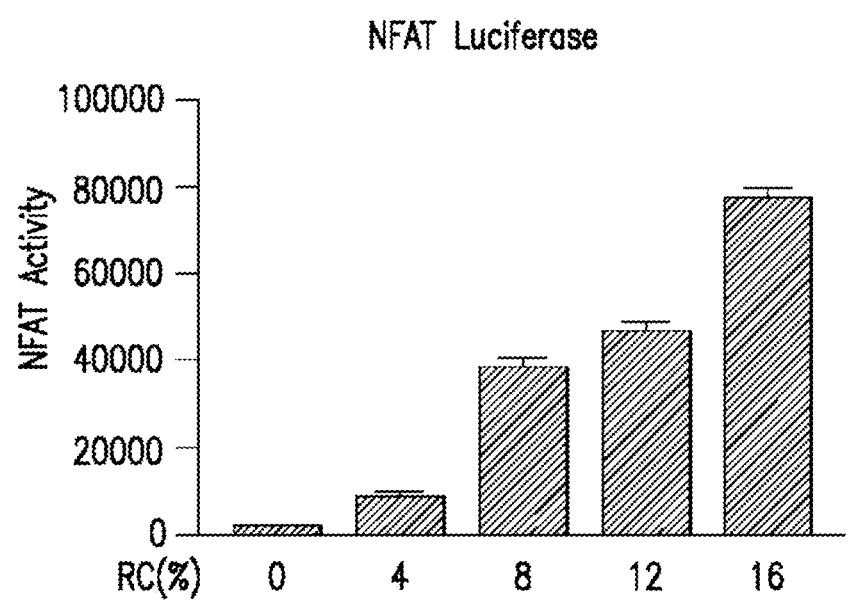

FIG. 2. NFAT (Nuclear Factor of Activated T-cells) activity in MDCK cells measured via NFAT-luciferase expression at increasing concentrations of radiocontrast.

Figure 3:
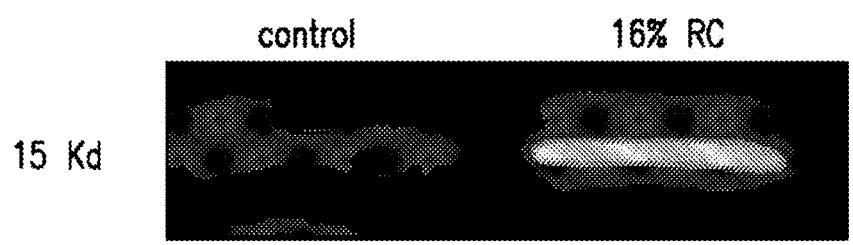

FIG. 3. Expression of calcineurin isoform CnB1 in control MDCK cells and MDCK cells exposed to 16% radiocontrast.

Figures 4A, 4B:
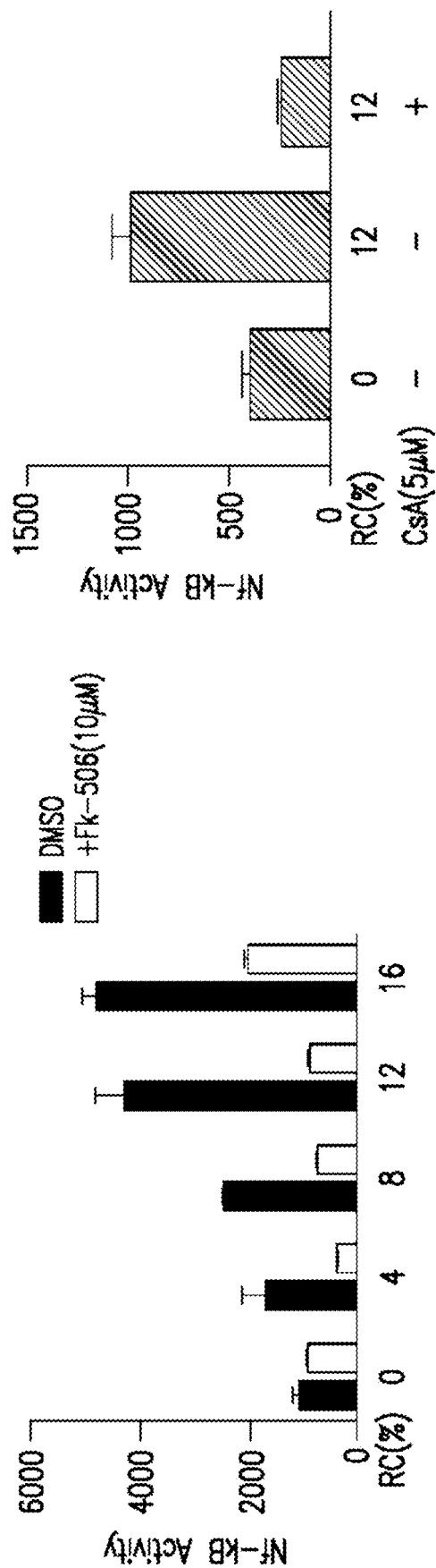

FIG. 4A-B. NFκB activity in MDCK cells exposed to increasing amounts of radiocontrast and treated with (A) FK506 (gray bar) or DMSO (as negative control, black bar) or (B) Cyclosporin A.

5. DETAILED DESCRIPTION

For clarity of description, and not by way of limitation, the detailed description is divided into the following subsections:
(a) radiocontrast agents;
(b) calcineurin inhibitors;
(c) radiocontrast medium compositions and kits; and
(d) methods of treatment.

5.1 Radiocontrast Agents

A radiocontrast medium for use according to the invention comprises, as one element, a radiocontrast agent. A radiocontrast agent is a composition that improves visibility of internal bodily structures in X-ray based imaging techniques such as, but not limited to, computerized tomography and radiography. As a particular, non-limiting example, a radiocontrast agent for use in a radiocontrast medium of the invention is an agent suitable for imaging of the kidney. In certain non-limiting embodiments, the radiocontrast agent contains iodine.

In non-limiting embodiments of the invention, the amount of radiocontrast agent is effective in promoting imaging in an imaging study.

In non-limiting embodiments of the invention, the radiocontrast agent is water soluble.

In non-limiting embodiments of the invention, the radiocontrast agent is non-ionic.

In non-limiting embodiments of the invention, the radiocontrast agent is a non-ionic monomer, for example, a low osmolality contrast agent, such as, but not limited to, iopamidol (Isovue®), iohexol (Omnipaque®), ioversol (Optiray™), iopromide (Ultravist®), ioxilan (Oxilan®), or iopentol (Imagopaque).

In non-limiting embodiments of the invention, the radiocontrast agent is a non-ionic dimer, for example, a low osmolality contrast agent, such as, but not limited to, iotrolan (Iotrol) or iodixonal (Visipaque™).

In non-limiting embodiments of the invention, the radiocontrast agent is an ionic radiocontrast agent.

In non-limiting embodiments of the invention, the radiocontrast agent is an iodine-based radiocontrast agent, e.g., iodinated.

In certain non-limiting embodiments the radiocontrast agent is a barium-based radiocontrast agent, e.g., barium sulfate.

In non-limiting embodiments of the invention, the radiocontrast agent is a gallium-based-radiocontrast agent, e.g., gallium 68 dotatate (NETSPOT®).

Non-limiting examples of radiocontrast agents include diatrizoate (Hypaque™ Gastrografin®), metrizoate (Isopaque), Iothalamate (Conray®), and ioxaglate (Hexabrix®). Additional non-limiting examples of radiocontrast agents are disclosed in U.S. Pat. No. 7,618,448, the contents of which are hereby incorporated by reference in their entirety.

5.2 Calcineurin Inhibitors

A second component of a radiocontrast medium of the invention is one or more calcineurin inhibitor, which may inhibit the action of calcineurin directly or indirectly. In a specific non-limiting embodiment, the calcineurin which is inhibited is human calcineurin.

In non-limiting embodiments of the invention, the amount of calcineurin inhibitor present in a radiocontrast medium of the invention is effective in decreasing the risk and/or extent of RIN in a subject.

In non-limiting embodiments of the invention, the amount of calcineurin inhibitor present, together with an antioxidant, in a radiocontrast medium of the invention is, s together with the antioxidant, effective in decreasing the risk and/or extent of nephropathy in a subject.

In non-limiting embodiments of the invention, the amount of calcineurin inhibitor present produces a local concentration in the kidney that reduces radiocontrast-mediated increase in NF-κB (nuclear factor of kappa light chain enhancer B) and/or NFAT (Nuclear Factor of Activated T-cells) activity by at least about 20 percent or at least about 30 percent in a kidney epithelial cell culture (e.g., MDCK cells or a human-based counterpart thereof).

In certain non-limiting embodiments, the calcineurin inhibitor is cyclosporine A (also referred to as cyclosporine herein).

In certain non-limiting embodiments, the calcineurin inhibitor is FK506 (tacrolimus).

In certain non-limiting embodiments, the calcineurin inhibitor is pimecrolimus (Elidel®).

In certain non-limiting embodiments, the calcineurin inhibitor is a cyclosporine analog, for example and not by way of limitation, voclosporin.

In non-limiting embodiments of the invention, the calcineurin inhibitor may be present in a radiocontrast medium in an amount that results in a local concentration of at least about 5 µM, at least about 10 µM, at least about 15 µM, at least about 20 µM, at least about 25 µM, at least about 30 µM, at least about 35 µM, at least about 40 µM, or between about 5 µM and about 10 µM, or between about 5 µM and about 20 µM, or between about 5 µM and about 30 µM, or between about 5 µM and about 40 µM, or between about 10 µM and about 20 µM, or between about 10 µM and about 30 µM, or between about 10 µM and about 40 µM, or between about 20 and about 30 µM, or between about 20 and about 40 µM, or between about 30 and about 40 µM, and/or up to about 10 µM and/or up to about 20 µM and/or up to about 30 µM or up to about 40 µM.

In non-limiting embodiments of the invention, where the calcineurin inhibitor is cyclosporine A, the amount of cyclosporine A comprised in a radiocontrast medium of the invention may be an amount that results in a local concentration of at least about 5 µM, or at least about 10 µM, or at least about 16 µM, or about 10 µM, or about 16 µM, or between about 5 µM and about 10 µM, or between about 5 and about 20 µM, or between about 10 and about 20 µM, and/or up to about 20 µM or up to about 30 µM.

In non-limiting embodiments of the invention, where the calcineurin inhibitor is FK506, the amount of FK506 comprised in a radiocontrast medium of the invention may be an amount that results in a local concentration of at least about 10 µM, or at least about 20 µM, or at least about 30 µM or about 20 µM, or about 24 µM, or between about 10 and about 40 µM, or between about 20 and about 30 µM, and/or up to about 30 µM or up to about 40 µM.

5.3 Radiocontrast Medium Compositions and Kits

In non-limiting embodiments, the present invention provides for a radiocontrast medium for use according to the invention comprising (i) a radiocontrast agent and (ii) a calcineurin inhibitor, in amounts effective in radioimaging in a subject with reduced risk and/or limited extent of RIN (should it occur) relative to the radiocontrast agent administered without the calcineurin inhibitor. Non-limiting examples of suitable radiocontrast agents and calcineurin inhibitors are set forth in the sections above.

In certain non-limiting embodiments, the present invention provides for a composition and/or a kit comprising an effective amount of a radiocontrast agent and calcineurin inhibitor disclosed herein, combined with a pharmaceutically acceptable carrier, e.g., an excipient. For example, and not by way of limitation, the present invention provides for a composition and/or a kit comprising the radiocontrast medium disclosed herein, further comprising a physiologically suitable solvent such as water, and optionally further comprising one or more formulating agents such as, but not limited to, a buffer and/or a preservative. In certain embodiments, the radiocontrast medium and/or kit does not include an antioxidant (i.e. in an amount effective to exert a significant antioxidant effect, and not a de minimis amount).

A "Pharmaceutically acceptable carrier," as used herein, includes any carrier which does not interfere with the effectiveness of the biological activity of the active ingredients and/or that is not toxic to the patient to whom it is administered. An excipient can be an excipient described in the Handbook of Pharmaceutical Excipients, American Pharmaceutical Association (1986). Non-limiting examples of suitable excipients can include a buffering agent, a preservative, a stabilizer, a binder, a compaction agent, a lubricant, a chelator, a dispersion enhancer and a disintegration agent.

In certain embodiments, an excipient can be a buffering agent. Non-limiting examples of suitable buffering agents can include sodium citrate, magnesium carbonate, magnesium bicarbonate, calcium carbonate, and calcium bicarbonate. As a buffering agent, sodium bicarbonate, potassium bicarbonate, magnesium hydroxide, magnesium lactate, magnesium glucomate, aluminium hydroxide, sodium citrate, sodium tartrate, sodium acetate, sodium carbonate, sodium polyphosphate, potassium polyphosphate, sodium pyrophosphate, potassium pyrophosphate, disodium hydrogen phosphate, dipotassium hydrogen phosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide and other calcium salts or combinations thereof can be used in a pharmaceutical formulation.

Non-limiting examples of suitable pharmaceutically acceptable carriers include one or more of phosphate buffered saline solutions, water, emulsions, such as oil/water emulsions, various types of wetting agents and sterile solutions. Additional non-limiting examples of pharmaceutically compatible carriers may include gels, bioadsorbable matrix materials, a buffering agent, a stabilizer, an antioxidant, a binder, a diluent, a dispersing agent, a rate controlling agent, a lubricant, a glidant, a disintegrant, a plasticizer, a preservative, implantation elements containing a composition comprising one or more of a radiocontrast agent and a calcineurin inhibitor, delivery or dispensing means or material. Such carriers can be formulated by conventional methods and may be administered to the subject at an effective amount. In certain embodiments, a pharmaceutically acceptable carrier may be one or more of disodium hydrogen phosphate dihydrate, sodium dihydrogen phosphate dihydrate, sodium chloride, myo-inositol and sorbitol.

In certain non-limiting embodiments, a calcineurin inhibitor and/or an antioxidant may be added to a commercial formulation of a radiocontrast agent.

In certain non-limiting embodiments, a pharmaceutical composition of the present invention is suitable for local instillation directly into the kidney, for example, but not limited to, as an aqueous solution or emulsion. In certain non-limiting embodiments, the pharmaceutical composition is suitable for rectal administration (for example, but not limited to, a suppository). The amounts of calcineurin inhibitor present in a pharmaceutical composition of the present invention is effective in reducing the risk and/or limiting the extent of RIN.

In non-limiting embodiments of the invention, a calcineurin inhibitor is present in a radiocontrast medium of the invention or composition thereof at an amount that is effective in decreasing the risk of RIN in a subject and/or limit the extent of RIN (should it occur).

In non-limiting embodiments of the invention, the amount of calcineurin inhibitor present in a radiocontrast medium of the invention or a composition thereof produces a local concentration in the kidney that reduces radiocontrast-mediated increase in NF-κB (nuclear factor of kappa light chain enhancer B) and/or NFAT activity by at least about 20 percent or at least about 30 percent in an acinar cell culture.

In non-limiting embodiments of the invention, the calcineurin inhibitor may be present in a radiocontrast medium in an amount that results in a local concentration of at least about 5 µM, at least about 10 µM, at least about 15 µM, at least about 20 µM, at least about 25 µM, at least about 30 µM, at least about 35 µM, at least about 40 µM, or between about 5 µM and about 10 µM, or between about 5 µM and about 20 µM, or between about 5 µM and about 30 µM, or between about 5 µM and about 40 µM, or between about 10 µM and about 20 µM, or between about 10 µM and about 30 µM, or between about 10 µM and about 40 µM, or between about 20 and about 30 µM, or between about 20 and about 40 µM, or between about 30 and about 40 µM, and/or up to about 10 µM and/or up to about 20 µM and/or up to about 30 µM or up to about 40 µM.

In non-limiting embodiments of the invention, where the calcineurin inhibitor is cyclosporine A, the amount of cyclosporine A comprised in a radiocontrast medium of the invention or a composition thereof may be an amount that results in a local concentration of at least about 5 µM, or at least about 10 µM, or at least about 16 µM, or about 10 µM, or about 16 µM, or between about 5 µM and about 10 µM, or between about 5 and about 20 µM, or between about 10 and about 20 µM, and/or up to about 20 µM or up to about 30 µM.

In non-limiting embodiments of the invention, where the calcineurin inhibitor is FK506, the amount of FK506 comprised in a radiocontrast medium of the invention or a composition thereof may be an amount that results in a local concentration of at least about 10 µM, or at least about 20 µM, or at least about 30 µM or about 20 µM, or about 24 µM, or between about 10 and about 40 µM, or between about 20 and about 30 µM, and/or up to about 30 µM or up to about 40 µM.

In certain non-limiting embodiments, the present invention provides for a kit comprising therapeutic amounts of (i) a radiocontrast agent and (ii) a calcineurin inhibitor, which may be combined prior to use.

In certain non-limiting embodiments, the present invention provides for a kit comprising therapeutic amounts (for use in kidney imaging) of (i) a radiocontrast agent and (ii) a calcineurin inhibitor, which may be provided in separate vials and administered separately, or in combination, to the subject being treated.

In certain non-limiting embodiments, the invention provides for a composition or kit for use in reducing the risk and/or limit the extent of RIN, should it occur, in a subject in need of such treatment, comprising a radiocontrast agent and a calcineurin inhibitor. In certain embodiments, a kit of the present invention further provides instructions indicating the use of the radiocontrast agent and the calcineurin inhibitor together or separately for kidney imaging.

In certain non-limiting embodiments, the invention provides for a kit comprising a vial comprising a radiocontrast agent and a vial comprising a calcineurin inhibitor with instructions to use any combination of the one or more vials together or separately for reducing the risk of RIN and/or limit the extent of RIN in a subject, should it occur. For example, and not by way of limitation, the instructions may indicate the administration of the radiocontrast agent and calcineurin inhibitor separately. Alternatively, or additionally, the instructions may indicate the mixing of the radiocontrast agent and calcineurin inhibitor together prior to administration. In certain embodiments, the instructions can include a description of a radiocontrast agent and a calcineurin inhibitor, and, optionally, other components included in the kit, and methods for administration, including methods for determining the proper state of the subject, the proper dosage amount and the proper administration method for administering one or more of a radiocontrast agent and a calcineurin inhibitor. Instructions can also include guidance for monitoring the subject over the duration of the treatment time.

Optionally, the kit may further comprise one or more vials comprising one or more of an antioxidant, atropine, calcitonin, somatostatin, glucagon and/or flurouracil, one or more protease-inhibiting drug such as aprotinin, gabexate masylate, camostate, and/or phospholipase A2, one or more anti-inflammatory agent such as allopurinol, a prostaglandin inhibitor, a platelet activating factor antagonist, a platelet activator factor acetyl hydrolase, or Lexipant, an antibiotic, and/or an anti-metabolite such as 5-flurouracil. For example, and not by way of limitation, a kit of the present invention may further comprise an antioxidant, e.g., in a separate vial.

In certain non-limiting embodiments, a kit of the present invention may further include one or more of the following: devices and additional reagents, and components, such as tubes, containers, cartridges, and syringes for performing the methods disclosed below.

In certain embodiments, a kit of this disclosure can further include a device for administering one or more of a radiocontrast agent and a calcineurin inhibitor to a subject, or a device for administering an additional agent or compound to a subject.

5.4 Methods of Treatment

According to the present invention, a radiocontrast medium according to the invention may be used instead of conventional imaging medium in an imaging procedure to reduce the risk and/or extent of RIN relative to the risk in a control subject where the imaging procedure was performed using conventional imaging medium without a calcineurin inhibitor. For example, and not by way of limitation, the control subject may have a similar clinical profile as the treated subject.

RIN is an impairment of renal function attributable to administration of radiocontrast. For example, but not by way of limitation, RIN may occur within 24 to 48 or up to about 72 hours after radiocontrast administration and may be associated with at least about a 25 percent increase in serum creatinine and/or at least about a 0.5 mg/dL increase in the absolute serum creatinine value. See, e.g., Andreucci et al., 2014, Biomed. Res. Int. Volume 2014, Article ID 362725, citing Thomsen and Morcos, 2003, Br. J. Radiol. 76(908): 513-518, and Mehran and Nikolsky, Kidney Int. Suppl., 2006, (100):S11-S15; and Silver et al., BMJ., 2015; 351: h4395. In certain non-limiting embodiments, reducing the extent of RIN includes a clinical scenario in which a subject, after receiving a kidney imaging procedure comprising administering a radiocontrast agent and a calcineurin inhibitor, within 24 to 48 hours or up to 72 hours after radiocontrast administration, does not exhibit an increase in serum creatinine of 25 percent or more or exhibit an increase of 20 percent or more or exhibit an increase of 15 percent or more; and/or does not exhibit an increase of at least about 0.5 mg/dL in the absolute serum creatinine value or exhibit an increase of at least about 0.3 mg/dL in the absolute creatinine value.

In non-limiting embodiments, the invention provides for a method of radioimaging a kidney in a subject, comprising introducing, into the kidney, a radiocontrast medium as set forth above, or pharmaceutical composition thereof, comprising (i) a radiocontrast agent and (ii) a calcineurin inhibitor, with the advantage that the subject would have a reduced risk of developing RIN or, if RIN should occur, its extent would be reduced, relative to a subject receiving radiocontrast agent without calcineurin inhibitor.

In non-limiting embodiments, the subject may be a human subject or a non-human subject such as a dog, a cat, a horse, a pig, a cow, a sheep, a goat, a mouse, a rat, a hamster, a guinea pig, or a rabbit. In certain embodiments, the subject is a human subject.

In non-limiting embodiments, a radiocontrast medium according to the invention may be used instead of conventional medium in an kidney imaging procedure to reduce the risk and/or limit the extent of RIN relative to the risk in a control subject where the imaging procedure was performed using conventional imaging medium without a calcineurin inhibitor.

The radiocontrast medium of the invention may be administered to the subject prior to or during an imaging procedure. It may be administered by injection or infusion or local instillation. Radiocontrast agent and calcineurin inhibitor may be administered together or separately to achieve the combination in the patient. In non-limiting embodiments, the calcineurin inhibitor may be administered orally.

Further to use of the radiocontrast medium of the invention, in certain embodiments, one or more of the following measures may be taken to further reduce risk of, and/or to limit damage by, RIN: (i) intravenous fluids may be administered before, during, and/or after the infusion of the radiocontrast medium; (ii) acetylcysteine may be administered, for example, prior to the infusion of radiocontrast medium, during the infusion of the radiocontrast medium, and/or after the infusion of the radiocontrast medium; and/or (iii) use of nonsteroidal anti-inflammatory drugs may be avoided.

In certain non-limiting embodiments, an effective amount of calcineurin inhibitor may be administered prior to infusion of radiocontrast medium, for example, but not limited to, within about 30 to about 60 minutes prior to infusion of the radiocontrast medium. In certain non-limiting embodiments, an effective amount of calcineurin inhibitor may be administered during and/or after the infusion of radiocontrast medium.

6. EXAMPLE: ACUTE USE OF CALCINEURIN PATHWAY INHIBITORS TO PREVENT RADIOCONTRAST-INDUCED NEPHROPATHY

To study the effect of radiocontrast on the kidney, $Ca^{2+}$ signals were meaured in Madin-Darby Canine Kidney ("MDCK") epithelial cells exposed to iohexol radiocontrast, as compared to unexposed control cells. The results are shown in FIG. 1A-B. MDCK cells exposed to 33 percent radiocontrast exhibited a sharp signal followed by a gradual decrease to baseline (FIG. 1B). Thapsigargin was administered at the timepoint shown as a positive control.

MDCK were engineered to contain a reporter for inflammatory NFAT activity. In particular, MDCK cells were infected with Ad-NFAT-luciferase and treated for 3 hours with 25-200 mg/L (0-16%) of iohexol radiocontrast. NFAT activity in MDCK cells was measured via NFAT-luciferase expression. 16 percent radiocontrast was observed to induce a 40-fold NFAT activation relative to control (FIG. 2).

Toward understanding the basis for these observations, the expression level of the calcineurin isoform, CnB1 was evaluated by Western blotting. As shown in FIG. 3, calcineurin isoform CnB1 expression was induced by radiocontrast in MDCK cells.

In further experiments, radiocontrast-induced NFκB inflammatory upregulation in MDCK cells was found to be dependent upon calcineurin, and could be inhibited by calcineurin inhibitors (FIG. 4A-B). NFκB activity in MDCK cells exposed to increasing amounts of radiocontrast and treated with either FK506 (FIG. 4A) or cyclosporin A (FIG. 4B). As shown in FIG. 4(A), MDCK cells treated with 16% radiocontrast exhibited an approximately 5-fold increase in NFκB activation. Pre-treatment with FK506 substantially reduced this increase. As shown in FIG. 4(B), cyclosporine A exhibited similar effects.

Various references are cited herein, the contents of which are hereby incorporated by reference in their entireties.

What is claimed:

1. A radiocontrast medium for use in radioimaging comprising (i) an iodinated radiocontrast agent; and (ii) a calcineurin inhibitor, in amounts effective to reduce risk of radiocontrast-induced nephropathy in a subject relative to the iodinated radiocontrast agent administered without the calcineurin inhibitor.

2. The radiocontrast medium of claim 1, wherein the iodinated radiocontrast agent is selected from the group consisting of diatrizoate, metrizoate, iothalamate, ioxaglate, and combinations thereof.

3. The radiocontrast medium of claim 1, wherein the iodinated radiocontrast agent is iohexol.

4. The radiocontrast medium of claim 1, wherein the calcineurin inhibitor is selected from the group consisting of cyclosporine, FK506 and combinations thereof.

5. The radiocontrast medium of claim 4, wherein the calcineurin inhibitor is cyclosporine.

6. The radiocontrast medium of claim 4, wherein the calcineurin inhibitor is FK506.

7. The radiocontrast medium of claim 1, wherein the radioimaging is a kidney imaging procedure.

8. A kit comprising a first vial comprising an iodinated radiocontrast agent and a second vial comprising a calcineurin inhibitor, in amounts effective to reduce risk of radiocontrast-induced nephropathy in a subject relative to the iodinated radiocontrast agent administered without the calcineurin inhibitor.

9. A pharmaceutical composition comprising the radiocontrast medium of claim 1 and one or more pharmaceutically acceptable carriers.

10. The pharmaceutical composition of claim 9, further comprising an antioxidant.

11. The pharmaceutical composition of claim 9, wherein the pharmaceutical composition does not contain an antioxidant.

12. A method of reducing risk of developing radiocontrast-induced nephropathy in a subject in need of radioimaging, the method comprising using, as an agent for radioimaging the subject, a radiocontrast medium comprising (i) an iodinated radiocontrast agent; and (ii) a calcineurin inhibitor in amounts such that the risk of radiocontrast-induced nephropathy in the subject is reduced.

13. A method of reducing extent of radiocontrast-induced nephropathy in a subject in need of radioimaging, the method comprising using, as an agent for radioimaging the subject, a radiocontrast medium comprising (i) an iodinated radiocontrast agent; and (ii) a calcineurin inhibitor in amounts such that the extent of radiocontrast-induced nephropathy in the subject is reduced.

* * * * *